US008367327B1

(12) United States Patent
Sagripanti et al.

(10) Patent No.: US 8,367,327 B1
(45) Date of Patent: Feb. 5, 2013

(54) METHOD FOR SIMULTANEOUSLY DETECTING MULTIPLE BIOLOGICAL THREAT AGENTS

(75) Inventors: Jose-Luis Sagripanti, Bel Air, MD (US); Monica Carrera Zandomeni, Philadelphia, PA (US)

(73) Assignee: The United States of America as Represented by the Secretary of the Army, Washington, DC (US)

( * ) Notice: Subject to any disclaimer, the term of this patent is extended or adjusted under 35 U.S.C. 154(b) by 1214 days.

(21) Appl. No.: 12/154,237

(22) Filed: May 21, 2008

(51) Int. Cl.
*C12Q 1/68* (2006.01)
*C07H 21/04* (2006.01)
*C07H 21/02* (2006.01)

(52) U.S. Cl. ......... 435/6.1; 435/4; 435/91.2; 435/287.1; 435/287.2; 536/23.1; 536/24.32; 536/24.33; 424/204.1; 424/234.1; 422/50; 422/58; 422/82.05

(58) Field of Classification Search .................... 422/50, 422/58, 82.05; 424/204.1, 234.1; 435/4, 435/6, 91.2, 287.1, 287.2; 536/23.1, 24.32, 536/24.33
See application file for complete search history.

(56) References Cited

PUBLICATIONS

Wilson, W.J., et al. Molecular and Cellular Probes, vol. 16, pp. 119-127, 2002.*

* cited by examiner

*Primary Examiner* — Rodney P. Swartz
(74) *Attorney, Agent, or Firm* — Ulysses John Biffoni

(57) ABSTRACT

A multiplex PCR assay for simultaneously detecting biological threat agents whose genome is DNA or RNA, by using computational tools to identify a specific target sequence which is unique to a specific genus or species of organism and is also a conserved sequence within that group, selecting specific primer sets, creating a probe to label the target nucleic acid, extracting the target nucleic acid from a sample, amplifying the targeted nucleic acid to detectible levels and reading the presence or absence of the target nucleic acid simultaneously from all threat agents.

19 Claims, 7 Drawing Sheets
(1 of 7 Drawing Sheet(s) Filed in Color)

Figure 2

| Genome | Gene | Function | Primer name | Primer Sequence | Sequence No. | Length (bp) | Tm(2) | Quality(1) (0-120) | PCR Product (bp) |
|---|---|---|---|---|---|---|---|---|---|
| B. a. pXO1 | Protective antigen (pag) | Protective antigen | PAG_1F476_501 | tggatttcaagttgtactggaccgat | SEQ. ID No. 1 | 26 | 60 | 85 | 150 |
| | | | PAG_1R600_625 | tgtcacggtctggaaccgtaggtcc | SEQ. ID No. 2 | 26 | 66 | 118 | |
| B. a. pXO2 | CapB | capsule biosynthesis protein capb, (pxo2-58) | CAPB_1F954_977 | tgctgaccaatctaagcctgcgt | SEQ. ID No. 3 | 24 | 61 | 101 | 169 |
| | | | CAPB_1R1097_1122 | agcaaactgctcagtacgatcaac | SEQ. ID No. 4 | 26 | 62 | 117 | |
| Yersinia | irp1 | yersiniabactin biosynthetic protein | IRP1_1F5788_5813 | acccacctcattggctatggcggcgt | SEQ. ID No. 5 | 26 | 68 | 132 | 200 |
| | | | IRP1_1R5962_5987 | tcacgcgggatgtgatactccggcg | SEQ. ID No. 6 | 26 | 67 | 144 | |
| Francisella | CapB | capsule biosynthesis protein capB | CAPB_1F356_381 | agccactttgcaatcgctgtgtgag | SEQ. ID No. 7 | 26 | 63 | 112 | 230 |
| | | | CAPB_1R560_585 | agctgcgattagttctgagcctcggt | SEQ. ID No. 8 | 26 | 64 | 136 | |
| Burkholderia | wcbQ | putative capsular polysaccharide biosynthesis protein WcbQ | WCBQ_1F21_46 | tgccattgccctgtcatttgccgcag | SEQ. ID No. 9 | 26 | 67 | 115 | 260 |
| | | | WCBQ_1R255_280 | acaactgactgaacagactcaggtcg | SEQ. ID No. 10 | 26 | 61 | 101 | |
| Rickettsia | RP293 | VIRD4 PROTEIN (virD4) | RP293_1F | gcttatttagaggttatagagttcg | SEQ. ID No. 11 | 26 | 53 | 99 | 290 |
| | | | RP293_1R | acttcttgaggtaaaagtaaagctct | SEQ. ID No. 12 | 26 | | | |
| Coxiella burnetti | CBU1551 | dinucleoside polyphosphate hydrolase | CBU_1551_1F337_361 | cccaacgaaaccttgcgtgaggca | SEQ. ID No. 13 | 25 | 65 | 116 | 310 |
| | | | CBU_1551_1R621_646 | acgtctcgcttaaactcaacgacgtgg | SEQ. ID No. 14 | 26 | 60 | 107 | |
| Brucella | | BMEI1877 | BMEI1877_1F60_86 | cgatggcgtcatccatgtgctgggtg | SEQ. ID No. 15 | 26 | 68 | 142 | 330 |
| | | | BMEI1877_1R364_389 | agtttgagcatgatgccgacgaaagc | SEQ. ID No. 16 | 26 | 62 | 107 | |
| Escherichia | ECs0540 | putative outer membrane transport protein | ECS0540_1F574_599 | gcaggcctgaactcatcgtcggatga | SEQ. ID No. 17 | 26 | 65 | 120 | 350 |
| | | | ECS0540_1R898_923 | tcatcccaatacgagcggtcgctgg | SEQ. ID No. 18 | 26 | 66 | 136 | |
| Variola | G4R | G4R protein | VAR_1F182615_182640 | gcagcaccgtatacaccacccaatg | SEQ. ID No. 19 | 26 | 64 | 122 | 380 |
| | | | VAR_1R182969_182994 | acgtctccaacagacgtgtgtccggat | SEQ. ID No. 20 | 26 | 65 | 112 | |

Figure 3

| Genome | Gene | Function | Primer Name | Primer Sequence | Sequence No. | Length (bp) | Tm(?) | Quality (1) (0-120) | PCR Product (bp) |
|---|---|---|---|---|---|---|---|---|---|
| Variola | G1R | G1R protein | VAR_1F182815_182840 | gcagcccgtttacccanccaag | Seq. No. 19 | 26 | 64 | 112 | |
| | | | VAR_1R182965_182994 | aagtaccaaanpagtgtgctacg gct | Seq. No. 20 | 28 | 65 | | |
| Machupo | MACVsLgp2 | L protein | Mach-2F | catnacnppcnappatgc | Seq. No. 21 | 24 | 54 | 106 | 200 |
| | | | Mach-2R | gcnggccannagnctggngcc | Seq. No. 22 | 25 | 61 | 96 | |
| EEEV | EEEVgp3 | E1 protein | EEEV-1F | tndgdgtcagccgnacgt | Seq. No. 23 | 24 | 66 | 104 | 321 |
| | | | EEE-1R | cgngcggccgnngtgtccton | Seq. No. 24 | 22 | 63 | 118 | |
| Influenza | YLUAVAH HH9N2s2gp1 | polymerase PB1 | Flu-1F | accanggnnppgcngnancgga | Seq. No. 25 | 25 | 60 | 106 | 138 |
| | | | Flu-1R | gangccctnggnnccntogc | Seq. No. 26 | 20 | 60 | 68 | |
| VEEV | VEEVgp3 | putative nonstructural polyprotein precursor | VEEV-1F | gtngtcgncganpcg | Seq. No. 27 | 20 | 58 | 99 | 106 |
| | | | VEEV-1R | acagccangntccctcgtt | Seq. No. 28 | 21 | 62 | 110 | |
| Lassa | LASVsLgp2 | L polymerase | Lass-1F | atcatcgggtccnncnd | Seq. No. 29 | 20 | 57 | 73 | 245 |
| | | | Lass-1R | aanngngcangtngganccn | Seq. No. 30 | 26 | 62 | 96 | |
| RVFV | RVFVsMgp1 | M protein | 1F1288_1311 | atgaatgnancccatgnngncgna | Seq. No. 31 | 26 | 63 | 144 | 170 |
| | | | 1R1432_1457 | gcaggcaaannggcaangt | Seq. No. 32 | 24 | 65 | 130 | |
| Ebola Zaire | gene-NP AAND75041 | nucleoprotein | 1P1421_1446 | gcatngacngnntgatgcanggt | Seq. No. 33 | 26 | 67 | 150 | 304 |
| | | | 1R1699_1724 | cacngcnnccaantncangncaaega | Seq. No. 34 | 26 | 65 | 138 | |

| Genome | Gene | Function | Primer Name | Primer Sequence | Sequence No. | Length (bp) | Tm(2) | Quality (1) (0-120) | PCR Product (bp) |
|---|---|---|---|---|---|---|---|---|---|
| Junin | NP_899217.1 | L protein | 1F5094_5118 | [illegible] | Seq. No. 35 | 25 | 62 | 144 | 358 |
| | | | 1R5425_5448 | [illegible] | Seq. No. 36 | 24 | 59 | 93 | |
| Marburg | MARVgp1 | nucleoprotein | Marb-1F | [illegible] | Seq. No. 37 | 25 | 60 | 128 | 376 |
| | | | Marb-1R | [illegible] | Seq. No. 38 | 25 | 63 | 111 | |
| Yellow Fever | YP_325663.1 | putative polyprotein | YF-1F | [illegible] | Seq. No. 39 | 28 | 68 | 128 | 288 |
| | | | YF-1R | [illegible] | Seq. No. 40 | 28 | 68 | 118 | |
| Crimean Congo L | YP_325663.1 | putative polyprotein | CC-F | [illegible] | Seq. No. 41 | 23 | 67 | 106 | 549 |
| | | | CC-R | [illegible] | Seq. No. 42 | 24 | 57 | 106 | |
| Dengue | DENVgp1 | capsid protein (C)* | D1 | [illegible] | Seq. No. 43 | 28 | 61 | 88 | 611 |
| | | | D2 | [illegible] | Seq. No. 44 | 29 | 61 | 86 | |

(1) This abstract value of quality describes the level of primer/PCR successfulness; this value varies from 120 for the "perfect & ideal" to 5 for the "worst" primer combination
(2) The melting temperature is calculated using a formula based on nearest neighbour thermodynamic theory with unified dS, dH and dG parameters (Allawi and SantaLucia, 1997)

Figure 3A

RNA target Cycling conditions

| | PROGRAM | |
|---|---|---|
| | Temp | Time |
| 1st Denaturing | 95 C | 5 min |
| 2nd Denaturation | 94 C | 30sec |
| Annealing | 58 C | 20sec |
| Extension | 70 C | 45sec |
| Cycles | 30 | |
| Final Extension | 68C | 15 min |

DNA target Cycling conditions

| | PROGRAM | |
|---|---|---|
| | Temp | Time |
| 1st Denaturing | 95 C | 5 min |
| 2nd Denaturation | 94 C | 30sec |
| Annealing | 59 C | 30sec |
| Extension | 70 C | 60sec |
| Cycles | 30 | |
| Final Extension | 68C | 30 min |

Figure 4

METHOD FOR SIMULTANEOUSLY DETECTING MULTIPLE BIOLOGICAL THREAT AGENTS

GOVERNMENT INTEREST

The invention described herein may be manufactured, used, and licensed by or for the U.S. Government.

RELATED APPLICATIONS

U.S. patent application Ser. No. 11/546,741 entitled "A Method for Detecting a Biological Threat Agent Using a Solid State Hybridization and Naked Eye Visualization" was filed Oct. 12, 2006 by the same inventor, Sagripanti, as the present application.

FIELD OF INVENTION

This invention relates to methods for detection of biological threat agents, and more specifically to a method for simultaneously detecting multiple biological threat agents contemporaneously.

BACKGROUND OF THE INVENTION

Nucleic acid-based technologies are the mainstay of the Department of Defense (DOD), Department of Health Services (DHS), Department of Health and Human Services (HHS), and other government agencies' strategy to detect and identify biological threat agents. Nucleic acid-based methods, particularly polymerase chain reaction (PCR) amplification tests, have several advantages which include higher sensitivity and often lower cost than other approaches. However, PCR techniques target only one biological agent, requiring sequential or separate testing for each biological threat agent individually. It is desirable to have a testing method which allows identification of multiple threat agents simultaneously or within a contemporaneous testing period.

Currently, because several tests are required to detect and identify threat agents, prioritization of testing for biological threat agents must be based upon intelligent guesses. The limitations of this approach are highlighted by the former Soviet Union's doctrine of simultaneously releasing a "cocktail" of multiple threat agents during a biological attack.

SUMMARY OF THE INVENTION

A novel bioinformatics approach utilizing computational tools determines target nucleic acid sequences unique to a group of biological threat agents. This method further develops novel and separate primers and probes each of which are capable of simultaneously detecting a target nucleic acid sequence in the presence of the other primers and probes and each of which separately excludes non-target sequences in a multiplex assay. The method and the primers and probes, as well as a set of specific assay conditions identified herein, results in a multiplex assay capable of effectuating the PCR amplification process utilizing probes (primers) which will amplify and permit detection of different biological threat agents under a common set of conditions. A target nucleic acid is a non-infectious signature sequence corresponding to bacterial and viral agents whose genome is either deoxyribose nucleic acid (DNA) or ribose nucleic acid (RNA).

The probability to identify a DNA sequence specific to a particular bacterium and absent in other organisms is dramatically higher for bacterial genomes than the relatively smaller viral genomes. Therefore, the analyses carried out with viral genomes were adapted from the approaches used for bacterial genomes, according to the disparity in genome size between viruses and bacteria. To identify conserved genetic regions among all isolates of one viral species, the sequences were aligned using a DNA or RNA multiple sequence alignment software program computational tool. One commercial embodiment of such software is ClustalW software which uses a Windows interface. However, other software which operates on other platforms and performs a similar or equivalent function may also be used.

Once the target nucleic acids are identified, a primer corresponding to each target nucleic acid is obtained. A primer is a nucleic acid strand that serves as a starting point for DNA replication. The primer acts as the required starting sequence for replication by providing a starting point for DNA polymerase. A primer for a known nucleic acid sequence can be obtained in a number of ways. For example, there are many commercially available laboratory facilities that will produce a primer based on the identified target nucleic acid sequence. One example of such a commercial facility that produces primers is Invitrogen Corporation located in Carlsbad, Calif.

Once one or more primers are obtained, a probe is created from each primer. For the present invention, a probe is a primer with a particular molecule that is used as an identifier, or label, and which renders a target nucleic acid sequence detectible by a human with a device such as a real time PCR screen, or through the use of an electrophoresis (e.g., gel or capillary electrophoresis) method. Examples of probes include, but are not limited to nucleic acids in *Bacillus anthracis* [SEQ. ID NOS. 1-4], *Yersinia* [SEQ. ID NOS. 5-6], *Francisella* [SEQ. ID NOS. 7-8], *Burkholderia* [SEQ. ID NOS. 9-10], *Rickettsia* [SEQ. ID NOS. 11-12], *Coxiella* [SEQ. ID NOS. 13-14], *Brucella* [SEQ. ID NOS. 15-16], *Escherichia* [SEQ. ID NOS. 17-18], Variola [SEQ. ID NOS. 19-20], Venezuelan Equine Encephalitis virus (VEEV) [SEQ. ID NOS. 27-28], Influenza virus [SEQ. ID NOS. 25-26], Rift Valley Fever virus [SEQ. ID NOS. 31-32], Machupo virus [SEQ. ID NOS. 21-22], Lassa virus [SEQ. ID NOS. 29-30], Yellow Fever virus [SEQ. ID NOS. 39-40], Ebola virus [SEQ. ID NOS. 33-34], Eastern Equine Encephalitis virus (EEEV) [SEQ. ID NOS. 23-24], Junin virus [SEQ. ID NOS. 35-36], Marburg virus [SEQ. ID NOS. 37-38], Dengue virus [SEQ. ID NOS. 43-44], and Crimean Congo virus [SEQ. ID NOS. 41-42].

The probe is then allowed to bind with its target nucleic acid sequence, thereby rendering the target nucleic acid sequence detectable by combining a suspect sample in a vessel that is inserted in a thermocycler or functionally similar device. The binding of the probe to target nucleic acid sequence serves the function of both making the target nucleic acid sequence detectible (i.e., labeling) and serving as a primer for the Taq Polymerase to replicate the target nucleic acid sequence.

Once this is accomplished, the step of amplifying any target nucleic acid that has bound to the probe takes place. Amplifying is the step of reproducing the amount of nucleic acid present to a level which may be detectible by a human with a device such as a real time PCR screen, or with a detection method such as electrophoresis (e.g., gel or capillary electrophoresis).

Once the amplification step is complete, detecting of labeled target nucleic acid may occur. A target nucleic acid sequence may be made detectable (e.g., to emit a signal) either by the use of a labeled primer (before amplification), by labeled nucleotides (incorporated during amplification), by labeled probes (after amplification), or by a combination thereof, without departing from the spirit of the present invention. Detecting may also be accomplished by using a real time PCR screen or a gel or capillary electrophoresis process, both of which are known in the art.

The probes or primers utilized in the exemplary embodiments of the invention described herein correspond to the following organisms referenced in FIG. 2: *Bacillus anthracis* [SEQ. ID NOS. 1-4], *Yersinia* [SEQ. ID NOS. 5-6], *Francisella* [SEQ. ID NOS. 7-8], *Burkholderia* [SEQ. ID NOS. 9-10], *Rickettsia* [SEQ. ID NOS. 11-12], *Coxiella* [SEQ. ID NOS. 13-14], *Brucella* [SEQ. ID NOS. 15-16], and *Escherichia* [SEQ. ID NOS. 17-18], Variola [SEQ. ID NOS. 19-20]; or as referenced in FIG. 3: VEEV [SEQ. ID NOS. 27-28], Influenza virus [SEQ. ID NOS. 25-26], Rift Valley Fever virus [SEQ. ID NOS. 31-32], Machupo virus [SEQ. ID NOS. 21-22], Lassa virus [SEQ. ID NOS. 29-30], Yellow Fever virus [SEQ. ID NOS. 39-40], Ebola virus [SEQ. ID NOS. 33-34], EEEV [SEQ. ID NOS. 23-24], Junin virus [SEQ. ID NOS. 35-36], Marburg virus (SEQ. ID NOS. 37-381 Dengue virus [SEQ. ID NOS. 43-44], and Crimean Congo virus [SEQ. ID NOS. 41-42].

Further embodiments of the invention may also include additional probes for each species within the genus provided, including but not limited to, Variola virus [SEQ. ID NOS. 19-20], *Bacillus* [SEQ. ID NOS. 1-4], *Yersinia* [SEQ. ID NOS. 5-6], *Francisella* [SEQ. ID NOS. 7-8], *Burkholderia* [SEQ. ID NOS. 9-10], *Brucella* [SEQ. ID NOS. 15-16], *Escherichia* [SEQ. ID NOS. 17-18], *Rickettsia* [SEQ. ID NOS. 11-12] or *Coxiella* genera [SEQ. ID NOS. 13-14] and other pathogenic organisms whose genome is DNA and VEEV [SEQ. ID NOS. 27-28], Influenza virus [SEQ. ID NOS. 25-26], Rift Valley Fever virus [SEQ. ID NOS. 31-32], Machupo virus [SEQ. ID NOS. 21-22], Lassa virus [SEQ. ID NOS. 29-30], Yellow Fever virus [SEQ. ID NOS. 39-40], Ebola virus [SEQ. ID NOS. 33-34], EEEV [SEQ. ID NOS. 23-24], Junin virus [SEQ. ID NOS. 35-36], Marburg virus [SEQ. ID NOS. 37-38], Dengue virus [SEQ. ID NOS. 43-44], Crimean Congo virus [SEQ. ID NOS. 41-42], and other pathogenic organisms whose genome is RNA.

GLOSSARY

Unless otherwise noted, or as may be evident from the context of their usage, any terms, abbreviations, acronyms or scientific symbols and notations used herein are to be given their ordinary meaning in the technical discipline to which the invention most nearly pertains. Abbreviations and acronyms (such as DNA, RNA, DOD, DHS, BLAST, etc.) may be used throughout the descriptions presented herein and should be given their generally understood meaning within the field unless contradicted or elaborated upon by other descriptions set forth herein. Some of the terms set forth below may be registered trademarks(®).

As used herein the term "PCR" is a polymerase chain reaction technique intended to replicate genetic material. This generally means the process of creating multiple copies of a nucleic acid sequence for detection.

As used herein the term "amplifying," "or "PCR amplification" is a step within the PCR process which generally means the process of creating multiple copies of a nucleic acid sequence for the purpose of creating a sufficient quantity of the labeled target nucleic acid to allow it to become detectable.

As used herein the term "detectable target nucleic acid" or "detectable target nucleic acid sequence" generally means a sufficient quantity of a labeled target nucleic acid as to be detected by a PCR method using a visual interface, by a process such as gel or capillary electrophoresis, or by any apparatus or process designed to perform the function of reading or identifying the presence of a specific nucleic acid.

As used herein the term "detecting" means determining the presence or absence or a target nucleic acid sequence. For example, detecting may occur by reading a banding pattern on gel or capillary electrophoresis, by reading an optical signal on a real time PCR screen or by any other device or method or, when applicable, by the human eye.

As used herein the term "labeled target nucleic acid" is a nucleic acid bound to substance (e.g., a moiety) that produces a detectible signal. There are several approaches to labeling a target nucleic acid to render it detectable by any of a variety of methods. For example, by a method using a visual interface, by a process such as gel or capillary electrophoresis, or by any apparatus or process designed to perform the function of reading or identifying the presence of a specific nucleic acid.

As used herein the term "Taq polymerase" or "DNA polymerase" is a thermostable enzyme which allows DNA to be replicated to copy the DNA strand and to allow a labeled nucleic acid to reach detectible levels, or any polymerase which serves an equivalent function, including any synthetically made polymerase.

As used herein the term "primer" is a nucleic acid strand, or a related molecule that serves as a starting point for DNA or RNA replication. A primer is required because DNA or RNA polymerases require a starting sequence, and cannot begin synthesizing a new DNA or RNA strand without a starting sequence. The primer acts as the required starting sequence, which enables the DNA or RNA polymerase to create a copy of the DNA or RNA strand.

As used herein the term "probe" is an oligonucleotide sequence such as the identified primers, or a related molecule that is made detectable by adhering to a particle selected from a group consisting of visible UV, fluorescent, radioactive, mass, electrochemical labels, or other molecules capable of being detected or rendering a nucleic acid capable of being detected. A probe may also serve the function of a primer in PCR amplification as long as the label does not hinder the ability of a polymerase to amplify the target. Examples of sequences that can be labeled and thus used also as probes include, but are not limited to nucleic acids in *Bacillus anthracis* [SEQ. ID NOS. 1-4], *Yersinia* [SEQ. ID NOS. 5-6], *Francisella* [SEQ. ID NOS. 7-8], *Burkholderia* [SEQ. ID NOS. 9-10], *Rickettsia* [SEQ. ID NOS. 11-12], *Coxiella* [SEQ. ID NOS. 13-14], *Brucella* [SEQ. ID NOS. 15-16], *Escherichia* [SEQ. ID NOS. 17-18], Variola [SEQ. ID NOS. 19-20], Venezuelan Equine Encephalitis virus (VEEV) [SEQ. ID NOS. 27-28], Influenza virus [SEQ. ID NOS. 25-26], Rift Valley Fever virus [SEQ. ID NOS. 31-32], Machupo virus [SEQ. ID NOS. 21-22], Lassa virus [SEQ. ID NOS. 29-30], Yellow Fever virus [SEQ. ID NOS. 39-40], Ebola virus [SEQ. ID NOS. 33-34], Eastern Equine Encephalitis virus (EEEV) [SEQ. ID NOS. 23-24], Junin virus [SEQ. ID NOS. 35-36], Marburg virus [SEQ. ID NOS. 37-38], Dengue virus [SEQ. ID NOS. 43-44], and Crimean Congo virus [SEQ. ID NOS. 41-42].

As used herein the term "sample" is a representative quantity of a suspect material. The material may be environmental, clinical, food, and all other contaminated surfaces found in civilian, military or other contexts.

As used herein the term "target nucleic acid" or "target nucleic acid sequence" is the genetic material intended to bind with the primer/probe allowing for PCR to effectively replicate the strand to which it is affixed. A target nucleic acid sequence may include DNA or RNA.

As used herein the term "real time PCR screen" or "screen" is a method of performing PCR wherein the final product is identified using an emitter and a detector instead of gel or capillary electrophoresis.

As used herein the term "computational tool" is any software or hardware used to compare nucleic acid sequences from organisms for the purpose of identifying a specific nucleic acid or nucleic acid sequence. Examples of computational tools are Perl Programming Language, software accommodating Basic Local Alignment Search Tools (BLAST), graphical software, spread sheet software, detection software, multiple sequence alignment software (e.g. ClustalW software), and functionally similar software as well as combinations thereof.

As used herein the term "conserved gene" or "conserved sequence" is a gene or DNA or RNA sequence that is unique to a particular species of genus or organism, and resistant to mutation.

As used herein the term "multiplex assay" is an assay which is capable of simultaneously detecting more than one threat agent present in a sample.

BRIEF DESCRIPTION OF THE DRAWINGS

The operation, and advantages of the present invention will become apparent upon consideration of the description herein taken in conjunction with the accompanying figures, which includes a color drawing (FIG. 5). Copies of this patent or patent application publication with color drawing(s) will be provided by the Office upon request and payment of the necessary fee. The figures are intended to be illustrative, not limiting. Certain elements in some of the figures may be omitted, or illustrated not-to-scale, for illustrative clarity.

In the drawings accompanying the description that follows, both reference numerals and legends (labels, text descriptions) may be used to identify elements. If legends are provided, they are intended merely as an aid to the reader, and should not in any way be interpreted as limiting.

Although the invention is generally described in the context of these preferred embodiments, it should be understood that the figures are not intended to limit the spirit and scope of the invention to these particular embodiments.

Figure 1:
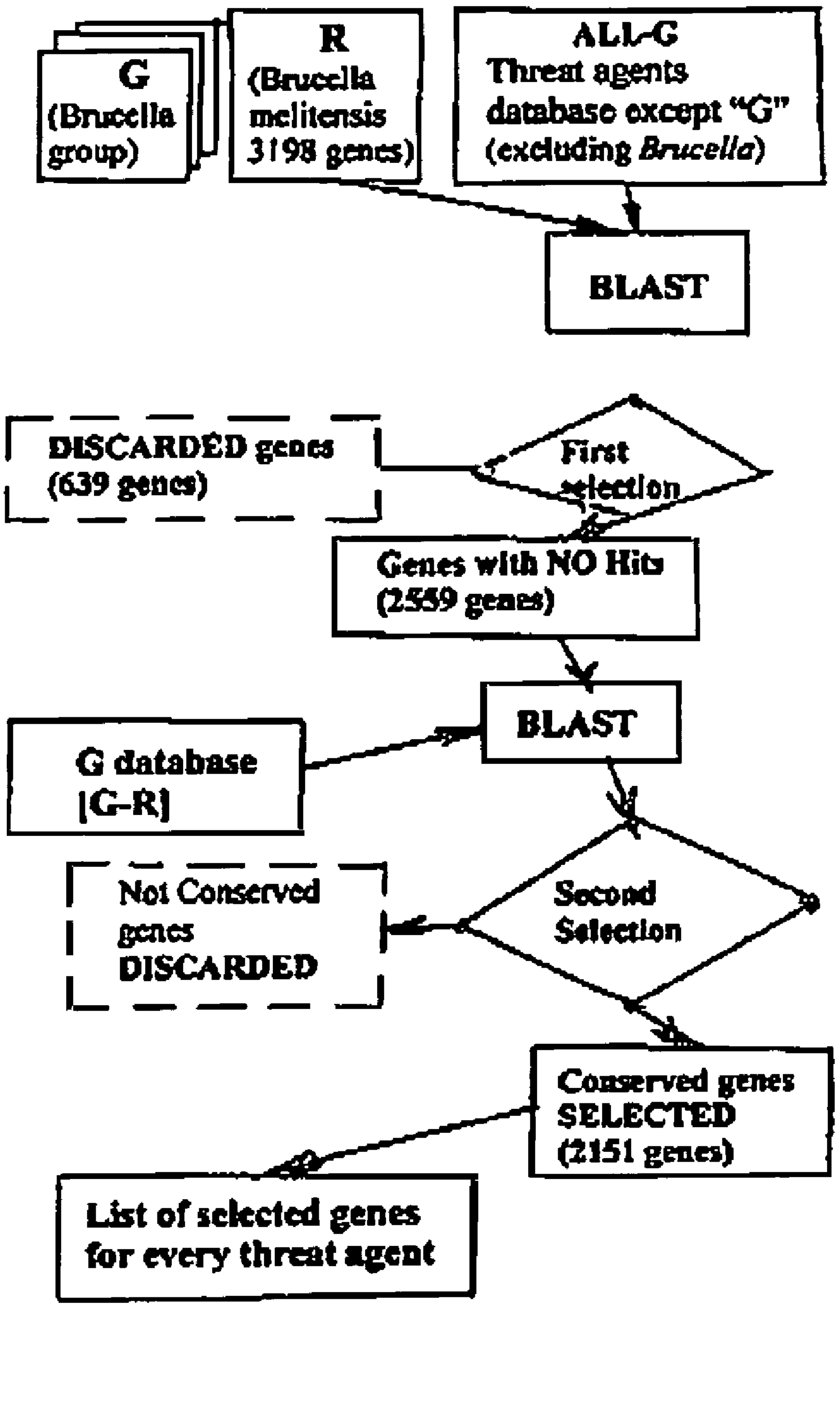

The structure, operation, and advantages of the present preferred embodiment of the invention will become further apparent upon consideration of the following description taken in conjunction with the accompanying figures. The figures submitted include the following:

FIG. 1 is a flowchart of an exemplary embodiment of a bioinformatics method for identifying DNA and RNA target nucleic acid sequences.

FIG. 2 is a table of primers derived from the DNA target nucleic acid sequences.

FIGS. 3 and 3A are tables of primers derived from the RNA target nucleic acid sequences.

FIG. 4 is a table illustrating exemplary DNA and RNA cycling conditions.

Figure 5:
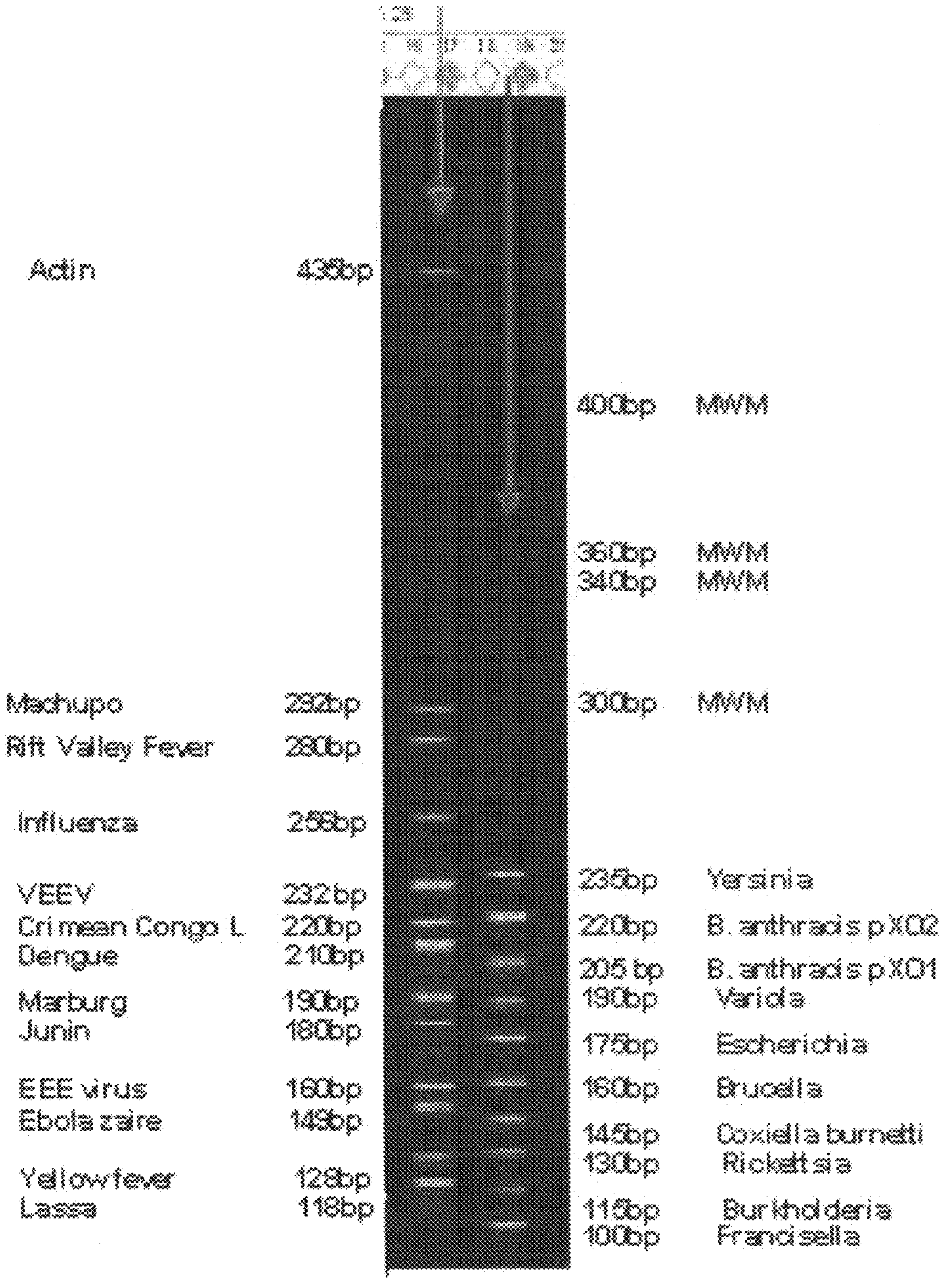

FIG. 5 is an illustration of an electrophoresis banding pattern achieved by using one embodiment of the method described herein.

Figure 6:
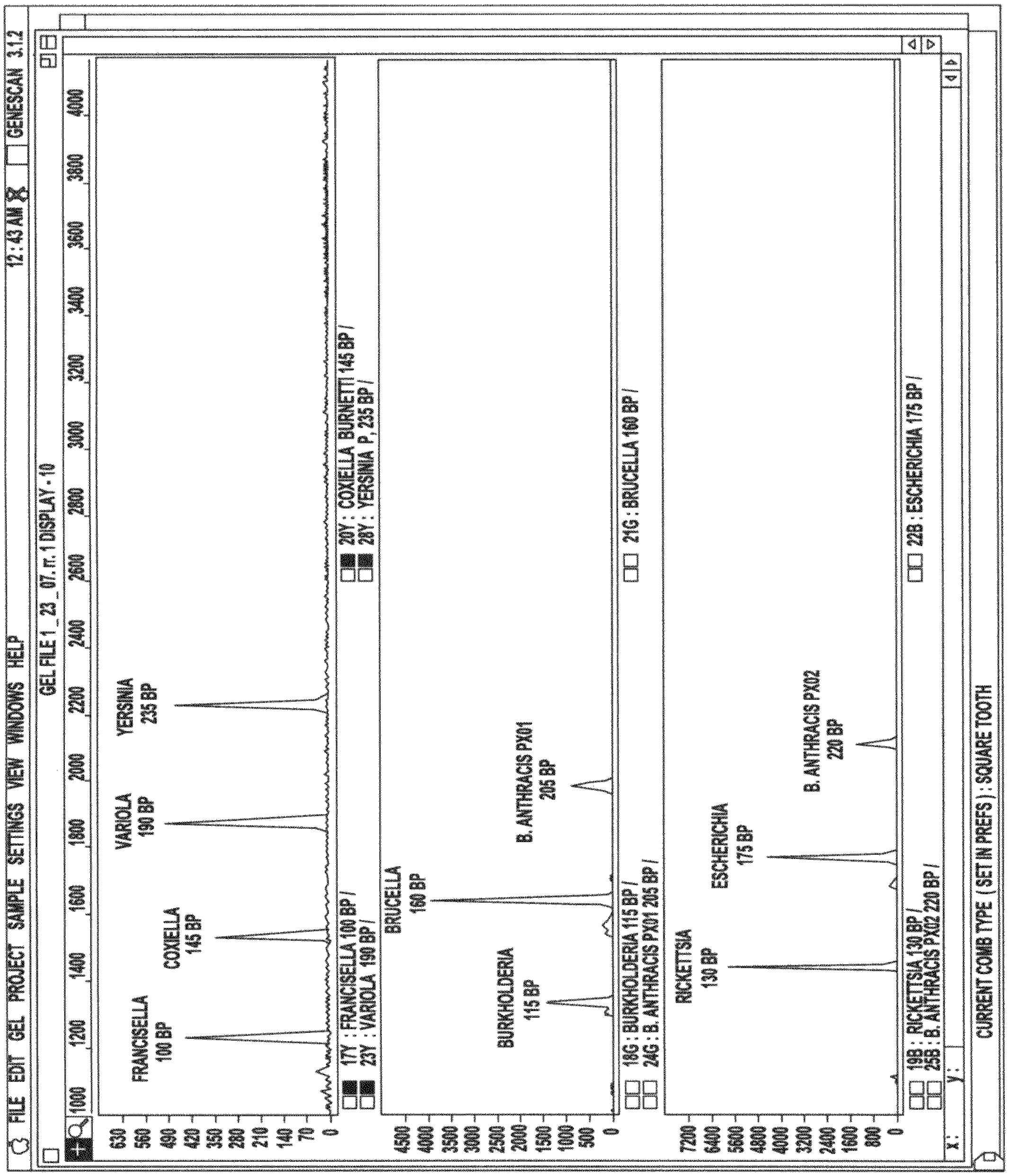

FIG. 6 is an illustration of one exemplary embodiment which uses capillary gel electrophoresis.

DETAILED DESCRIPTION OF PREFERRED EMBODIMENTS OF INVENTION

Embodiment Using Screen

In one exemplary embodiment, a target nucleic acid is amplified utilizing a real time PCR method and identification.

In this exemplary embodiment, a computational tool is used to manipulate strings of data representing the genetic code of several organisms. In the embodiment illustrated in FIG. 1, the Perl programming language is used in combination with BLAST. It should be noted that other embodiments of this method may use different or additional computational tools, or may include additional or equivalent procedures for manipulation and analysis of data strings and still be within the scope of the method described herein.

The data obtained is represented by a list of consecutive characters (sequences) and compared to biological information modules in the computational tool to identify specific gene sequences. The specific gene sequences must meet two criteria simultaneously: (a) the gene sequence is absent in every species but the one being studied; and (b) the gene sequence is unique within the organism's own species group and/or genus (i.e., a conserved gene). Meeting these requirements will ensure that said sequence does not cross-react with other sequence's primers and probes during PCR. Each target nucleic acid sequence is to be compared against all other species' genomes to fulfill the first criteria stated above.

For example, in one embodiment, *Brucella* [SEQ. ID NOS. 15-16] may be the agent desired to be identified in combination with other biological threat agents. Various other exemplary embodiments may be directed toward any combination of Variola virus [SEQ. ID NOS. 19-20], *Bacillus* [SEQ. ID NOS. 1-4], *Yersinia* [SEQ. ID NOS. 5-6], *Francisella* [SEQ. ID NOS. 7-8], *Burkholderia* [SEQ. ID NOS. 9-10], *Brucella* [SEQ. ID NOS. 15-16], *Escherichia* [SEQ. ID NOS. 17-18], *Rickettsia* [SEQ. ID NOS. 11-12] or *Coxiella* genera [SEQ. ID NOS. 13-14] and other pathogenic organisms whose genome is DNA and VEEV [SEQ. ID NOS. 27-28], Influenza virus [SEQ. ID NOS. 25-26], Rift Valley Fever virus [SEQ. ID NOS. 31-32], Machupo virus [SEQ. ID NOS. 21-22], Lassa virus [SEQ. ID NOS. 29-30]; Yellow Fever virus [SEQ. ID NOS. 39-40], Ebola virus [SEQ. ID NOS. 33-34], EEEV [SEQ. ID NOS. 23-24], Junin virus [SEQ. ID NOS. 35-36], Marburg virus [SEQ. ID NOS. 37-38], Dengue virus [SEQ. ID NOS. 43-44], Crimean Congo virus [SEQ. ID NOS. 41-42], and other pathogenic organisms whose genome is RNA.

In the exemplary embodiments, each threat agent is compared to all other species using BLAST to determine the target nucleic acid sequence unique to all organisms within a species or genus of biological threat agents. Once the target nucleic acid sequence is determined to be unique to one group a second comparison, or BLAST, is created to compare the target nucleic acid sequence to other members of the same group. This is intended to determine whether or not the gene sequence is a conserved gene, thus fulfilling the second criteria. In addition, a third comparison of potentially useful target sequences against every known sequence of all known organisms in genomic databases (like Genbank) allows discarding additional potential sequences whose targeting could compromise specificity of the assay.

Once these target nucleic acid sequences are determined, a primer can be created to bind to the target nucleic acid sequence. FIG. 2 and FIG. 3 are tables of novel and exemplary applicable primers for this invention. Additional primers may become available with the advancement of computational tools.

In the first exemplary embodiment, the primers (having one end being the 3' end and the other end being the 5' end) are labeled at the 5' end with a fluorescent, colorimetric, or radioactive marker to produce a probe. In the embodiment shown, examples of labels are latex particles, 6-carboxy-fluorescein (FAM) blue, tetrachloro-6-carboxy-fluorescein (TET) green, hexachloro-6-carboxy-fluorescein (HEX) yellow, and other appropriate markers.

In the first exemplary embodiment, a sample from a contaminated surface is obtained. The sample is sonicated. The sonification procedure is well known to those skilled in the art, and is intended to lyse (destroy) any cells present in the sample, thus releasing their genetic material (DNA or RNA). Sonication can be replaced by enzymatic lysis or other disruptive techniques that release cellular or viral nucleic acids without departing from the spirit of the invention.

In the first exemplary embodiment, the sample nucleic acid obtained from the sonification or equivalent procedure is now ready to be denatured (heated). The sample is placed into a conventional thermocycler or other device used for PCR. The thermocycler or other device is closed and programmed with the appropriate incubation information for the intended sample. In the first embodiment, a preliminary denaturation process denatures the sample and activates the polymerase used (sometimes referred to as a "Hot Start" polymerase). In the exemplary embodiment, the cycle is performed preferably at 95° C. and is performed for a period ranging from 5 to 10 minutes. Also, in the exemplary embodiment, once activation of the enzyme has been done, a cycling at three different temperatures is performed to amplify target sequences. FIG. 4 illustrates exemplary RNA and DNA cycling conditions that uniquely allow the amplification of every threat target to be amplified simultaneously, if present in a sample.

The sample of nucleic acid is first denatured between 85 and 99° C., preferably at 95° C. for 30 seconds to 30 minutes, preferably for 5 minutes. A second denaturation step at 1° C. lower performed for 10 seconds to 2 minutes, preferably for 30 seconds, improves nucleic acid denaturation and increases amplification yield later. This step can be omitted without departing from the spirit of the invention.

This step of denaturing the sample causes the helix of the sample of nucleic acid to break down and become accessible to primers. Primers, including but not limited to those corresponding to Variola virus [SEQ. ID NOS. 19-20], *Bacillus* [SEQ. ID NOS. 1-4], *Yersinia* [SEQ. ID NOS. 5-6], *Francisella* [SEQ. ID NOS. 7-8], *Burkholderia* [SEQ. ID NOS. 9-10], *Brucella* [SEQ. ID NOS. 15-16], *Escherichia* [SEQ. ID NOS. 17-18], *Rickettsia* [SEQ. ID NOS. 11-12] or *Coxiella* genera [SEQ. ID NOS. 13-14] as set out in FIG. 2, and VEEV [SEQ. ID NOS. 27-28], Influenza virus [SEQ. ID NOS. 25-26], Rift Valley Fever virus [SEQ. ID NOS. 31-32], Machupo virus [SEQ. ID NOS. 21-22], Lassa virus [SEQ. ID NOS. 29-30], Yellow Fever virus [SEQ. ID NOS. 39-40], Ebola virus [SEQ. ID NOS. 33-34], EEEV [SEQ. ID NOS. 23-24], Junin virus [SEQ. ID NOS. 35-36], Marburg virus [SEQ. ID NOS. 37-38], Dengue virus [SEQ. ID NOS. 43-44] and Crimean Congo virus genera [SEQ. ID NOS. 41-42] as set out in FIG. 3, and other pathogenic organisms whose genome is DNA or RNA, are added to the sample with the exposed target nucleic acid.

The mixture of target nucleic acid and primers each specific to one targeted organism is exposed to a process termed annealing whereby primers bind to complementary sequences in target nucleic acid if this is present in the sample sequences. The sample is cooled to temperatures ranging between 15° C. and 80° C., preferably at 58.5° C. for a period ranging between 5 seconds and 2 minutes, preferably 25 seconds; so that the target nucleic acid becomes double-stranded again with its conjugate primers.

Extension is now possible. Taq polymerases or equivalent polymerases and nucleotides are added to the mixture of double-stranded nucleic acid with its conjugate primers to complete the sequence. The resulting sample is incubated between 15 and 79° C., most preferably at 70° C. for 5 seconds to 5 minutes, most preferably for 45 to 60 seconds so that the Taq polymerases start the replication process at the primer and continue down the strand of DNA attaching nucleotides in sequence to duplicate genetic material. Departure from the disclosed conditions is feasible albeit with some loss of sensitivity for some of the targets. A wider range of conditions than those described above can be achieved by addition of detergents such as sodium- or lauryl-dodecylsulfate (SDS or LDS, respectively), formamide, chaootropic agents, enhancers, or other reagents that facilitate denaturing, annealing, extension, or other steps, without departing from the spirit of this invention In the first exemplary embodiment, the Taq polymerase is Promega Taq polymerase from Promega. Also according to the present invention, the Taq polymerase may be Accuprime Taq from Invitrogen or Hot Start from Quiagen.

In the first exemplary embodiment, the replication process is repeated between 10 and 60 cycles, preferably 30 cycles, to ensure that sufficient quantity of nucleic acid is obtained.

In the first exemplary embodiment, an emitter is used to excite the label on the corresponding DNA. This label emits radiation that is of sufficient quantity as to make it detectable. A conventional detector receives the radiation and determines if the amount present is of sufficient quantity to rule the sample positive for a biological threat agent. A positive screening sample may then be investigated by a further method (such as one of the following two embodiments) to identify a particular threat organism.

Embodiment Using Gel Electrophoresis

In a second exemplary embodiment, gel electrophoresis is used as an identification method. This second embodiment also uses the novel bioinformatics approach described in the previous embodiment. The second embodiment similarly uses computational tools to manipulate data strings representing the genetic code of several organisms, to identify target DNA and RNA sequences which are both conserved and unique to the organism.

In this embodiment, once target sequences are identified, primers are created to bind to the target nucleic acid sequence, and the same oligonucleotide sequences used as primers are labeled with markers to create probes including but not limited to those corresponding to *Bacillus anthracis* [SEQ. ID NOS. 1-4], *Yersinia [SEQ. ID NOS.* 5-6], *Burkholderia* [SEQ. ID NOS. 9-10, *Francisella* [SEQ. ID NOS. 7-8], *Rickettsia* [SEQ. ID NOS. 11-12], *Coxiella* [SEQ. ID NOS. 13-14], *Brucella* [SEQ. ID NOS. 15-16], *Escherichia* [SEQ. ID NOS. 17-18], Variola [SEQ. ID NOS. 19-20] and other organisms whose genome is DNA or Venezuelan Equine Encephalitis virus (VEEV) [SEQ. ID NOS. 27-28], Influenza virus [SEQ. ID NOS. 25-26], Rift Valley Fever virus [SEQ. ID NOS. 31-32], Machupo virus [SEQ. ID NOS. 21-22], Lassa virus [SEQ. ID NOS. 29-30], Yellow Fever virus [SEQ. ID NOS. 39-40], Ebola virus [SEQ. ID NOS. 33-34], Eastern Equine Encephalitis virus (EEEV) [SEQ. ID NOS. 23-24], Junin virus [SEQ. ID NOS. 35-36], Marburg virus [SEQ. ID NOS. 37-38], Dengue virus [SEQ. ID NOS. 43-44], and Crimean Congo virus [SEQ. ID NOS. 41-42] and others whose genome are RNA. (See FIGS. 2 and 3).

In the second exemplary embodiment, a sample is sonicated to lyse cells present and release their genetic material. The nucleic acid obtained is then denatured in a thermocycler or other device programmed with appropriate incubation information, allowing the helix of the sample of nucleic acid to become accessible to primers.

Once binding of the primers has occurred, the mixture is annealed and cooled so that the nucleic acid binds with its conjugate primers. Taq polymerases and nucleotides are added to complete the sequence. The replication process is repeated for a sufficient number of cycles to ensure that a sufficient quantity of nucleic acid is obtained.

In the second embodiment, DNA and RNA fragments are removed from the thermocycler and separated via gel electrophoresis. Gel electrophoresis is a process that is well known to anyone skilled in the art. The banding pattern on the gel is recorded and compared against the reference sample. If the DNA and RNA fragments are of correct size the organism may be identified. An exemplary banding pattern using this embodiment is shown in FIG. 5, which represents the reconstructed gel image of the electrophoresis run in a 377 ABI Prism Sequencer analyzer. The left arrow (green) indicates the sample corresponding to the RNA target multiplex amplification. The values shown on the left indicate the amplicon size and the corresponding RNA target pathogen. In the embodiment shown, Actin (435 bp) is the positive control for the Reverse Transcriptase included in the assay. The right (pink) arrow indicates the sample corresponding to the DNA target multiplex amplification. The values shown on the right indicate the amplicon size and the corresponding DNA target pathogen.

Embodiment Using Capillary Electrophoresis

In a third exemplary embodiment, capillary electrophoresis is used as an identification method. This third embodiment also uses the novel bioinformatics approach described in the previous embodiment. The third embodiment similarly uses computational tools to manipulate data strings representing the genetic code of several organisms, to identify target DNA sequences which are both conserved and unique to the organism.

In this embodiment, once target sequences are identified, primers are created to bind to the target nucleic acid sequence, and the same oligonucleotide sequences used as primers are labeled, with markers to create probes including but not limited to those corresponding to *Bacillus anthracis* [SEQ. ID NOS. 1-4], *Yersinia* [SEQ. ID NOS. 5-6], *Francisella* [SEQ. ID NOS. 7-8], *Burkholderia* [SEQ. ID NOS. 9-10], *Rickettsia* [SEQ. ID NOS. 11-12], *Coxiella* [SEQ. ID NOS. 13-14], *Brucella* [SEQ. ID NOS. 15-16], *Escherichia* [SEQ. ID NOS. 17-18], Variola [SEQ. ID NOS. 19-20] and other organisms whose genome is DNA or Venezuelan Equine Encephalitis virus (VEEV) [SEQ. ID NOS. 27-28], Influenza virus [SEQ. ID NOS. 2-26], Rift Valley Fever virus [SEQ. ID NOS. 31-32], Machupo virus [SEQ. ID NOS. 21-22], Lassa virus [SEQ. ID NOS. 29-30], Yellow Fever virus [SEQ. ID NOS. 39-40], Ebola virus [SEQ. ID NOS. 33-34], Eastern Equine Encephalitis virus (EEEV) [SEQ. ID NOS. 23-24], Junin virus [SEQ. ID NOS. 35-36], Marburg virus [SEQ. U) NOS. 37-38], Dengue virus [SEQ. ID NOS. 43-44], and Crimean Congo virus [SEQ. ID NOS. 41-42], and others whose genome are RNA. (See FIGS. 2 and 3).

In the third exemplary embodiment, a sample is sonicated to lyse cells present and release their genetic material. The nucleic acid obtained is then denatured in a thermocycler or other device programmed with appropriate incubation information, allowing the helix of the sample of nucleic acid to become accessible to primers. Once binding of the primers has occurred, the mixture is annealed and cooled, so that the nucleic acid becomes double-stranded again with its conjugate primers. Taq polymerases and nucleotides are added to complete the sequence. The replication process is repeated for a sufficient number of cycles to ensure that a sufficient quantity of nucleic acid is obtained.

In the third embodiment, DNA and RNA fragments are removed from the thermocycler and separated via capillary electrophoresis. The capillary electrophoresis process is well known to anyone skilled in the art. The banding pattern within the capillary tube is recorded and compared against the reference sample. If the DNA and RNA fragments are of correct size the organism may be identified. An exemplary banding pattern using this embodiment is shown in FIG. 6, which represents the reconstructed image of the capillary electrophoresis output from an ABI capillary sequence analyzer.

Although the invention has been shown and described with respect to a certain preferred embodiment or embodiments, certain equivalent alterations and modifications will occur to others skilled in the art upon the reading and understanding of this specification and the annexed drawings. In particular regard to the various methods and apparatus used in detecting multiple biological threat agents, the terms (including a reference to a "means") used to describe such detection are intended to correspond, unless otherwise indicated, to any methods or apparatus which perform the specified detection of the described multiple biological threat agents (i.e., that is functionally equivalent), even though not equivalent to the disclosed methods or apparatus which performs the function in the herein illustrated exemplary embodiments of the invention. In addition, while a particular feature of the invention may have been disclosed with respect to only one of several embodiments, such a feature may be combined with one or more features of the other embodiments as may be desired and advantageous for any given or particular application.

What is claimed is:

1. A method of creating a multiplex assay capable of detecting more than one biological threat agent simultaneously within a sample containing a mixture of biological threat agents and excluding non-targeted nucleic acid sequences within the sample, comprising the steps of:

(a) selecting more than one target nucleic acid sequence, wherein each of said more than one target nucleic acid sequence is unique to a specific genus or species of biological threat agent organism and is a conserved sequence within that group;

(b) obtaining more than one primer each of which corresponds to one of said more than one target nucleic acid sequence, wherein each of said more than one primer is selected from the group consisting of SEQ ID NOs. 1-44 and is specific to one biological threat agent;

(c) creating at least one probe from each of said more than one primer by labeling each of said more than one primer with a detectable label;

(d) binding at least one target nucleic acid sequence, if present within said sample, with said at least one probe to create at least one labeled target nucleic acid;

(e) amplifying said at least one labeled target nucleic acid, if present, to create at least one detectable nucleic acid; and (f) detecting a presence or absence of said at least one detectable nucleic acid.

2. The method of claim 1, wherein the organism is a bacterium.

3. The method of claim 1, wherein the organism is a virus.

4. The method of claim 1, wherein the target nucleic acid sequence is DNA.

5. The method of claim 1, wherein the target nucleic acid sequence is RNA.

6. The method of claim 1, wherein each of said more than one primer is selected from the group consisting of SEQ ID NOs. 1-20.

7. The method of claim 1, wherein each of said more than one primer is selected from the group consisting of SEQ ID NOs. 21-44.

8. The method of claim 1, wherein said at least one probe is created from a primer selected from the group consisting of SEQ ID NOs. 1-20.

9. The method of claim 1, wherein said at least one probe is created from a primer selected from the group consisting of SEQ ID NOs. 21-44.

10. The method of claim 1, wherein said at least one probe is made detectible by adhering or binding a particle or molecule selected from a group consisting of at least one visible, UV, fluorescent, radioactive, mass marker, and electrochemical label to said more than one primer, each of which is specific to one biological threat agent.

11. The method of claim 1, wherein said binding, amplification, and detecting is performed using a real time PCR screen.

12. The method of claim 1, wherein said detecting further comprises identifying said one or more biological threat agents within said sample by separating said at least one target nucleic acid sequence using an electrophoresis process and reading a banding pattern created by said electrophoresis process and comparing the banding pattern to a known reference pattern of nucleic acid segments of known size.

13. The method of claim 12, wherein the electrophoresis process is a gel electrophoresis.

14. The method of claim 12, wherein the electrophoresis process is a capillary electrophoresis.

15. A method of creating a multiplex assay capable of detecting more than one biological threat agent simultaneously within a sample and excluding non-targeted nucleic acid sequences within the sample, comprising the steps of:

(a) selecting more than one target nucleic acid sequence, wherein each of said more than one target nucleic acid sequence is unique to a specific genus or species of biological threat agent organism and is a conserved sequence within that group;

(b) obtaining more than one primer each of which corresponds to one of said more than one target nucleic acid sequence, each of said more than one primers being selected from a group consisting of SEQ ID Nos. 1-44;

(c) creating at least one probe from each of said more than one primer by labeling each of said more than one primer with a detectable label;

(d) binding the at least one target nucleic acid sequence, if present within said sample, with said at least one probe to create at least one labeled target nucleic acid;

(e) amplifying said at least one labeled target nucleic acid, if present, to create at least one detectable nucleic acid; and (f) detecting a presence or absence of said at least one detectable nucleic acid using a PCR amplification method selected from a group consisting of a real time PCR screen, gel electrophoresis and capillary electrophoresis.

16. The method of claim 15, wherein each of said more than one primer is selected from the group consisting of SEQ ID NOs. 1-20.

17. The method of claim 15, wherein each of said more than one primer is selected from the group consisting of SEQ ID NOs. 21-44.

18. The method of claim 15, wherein said at least one probe is created from a primer selected from the group consisting of SEQ ID NOs. 1-20.

19. The method of claim 15, wherein said at least one probe is created from a primer selected from the group consisting of SEQ ID NOs. 21-44.

* * * * *

SEQUENCE LISTING

```
<160> NUMBER OF SEQ ID NOS: 44

<210> SEQ ID NO 1
<211> LENGTH: 26
<212> TYPE: DNA
<213> ORGANISM: Bacillus anthracis

<400> SEQUENCE: 1

tggatttcaa gttgtactgg accgat                                  26


<210> SEQ ID NO 2
<211> LENGTH: 25
```

-continued

```
<212> TYPE: DNA
<213> ORGANISM: Bacillus anthracis

<400> SEQUENCE: 2

tgtcacggtc tggaaccgta ggtcc                                           25


<210> SEQ ID NO 3
<211> LENGTH: 23
<212> TYPE: DNA
<213> ORGANISM: Bacillus anthracis

<400> SEQUENCE: 3

tgctgaccaa tctaagcctg cgt                                             23


<210> SEQ ID NO 4
<211> LENGTH: 24
<212> TYPE: DNA
<213> ORGANISM: Bacillus anthracis

<400> SEQUENCE: 4

agcaaactgc tcagtacgat caac                                            24


<210> SEQ ID NO 5
<211> LENGTH: 26
<212> TYPE: DNA
<213> ORGANISM: Yersinia

<400> SEQUENCE: 5

acccacctca ttggctatgg cggcgt                                          26


<210> SEQ ID NO 6
<211> LENGTH: 25
<212> TYPE: DNA
<213> ORGANISM: Yersinia

<400> SEQUENCE: 6

tcacgcggga tgtgatactc cggcg                                           25


<210> SEQ ID NO 7
<211> LENGTH: 26
<212> TYPE: DNA
<213> ORGANISM: Francisella

<400> SEQUENCE: 7

agccactttt gcaatcgctg tgtgag                                          26


<210> SEQ ID NO 8
<211> LENGTH: 26
<212> TYPE: DNA
<213> ORGANISM: Francisella

<400> SEQUENCE: 8

agctgcgatt agttctgagc ctcggt                                          26


<210> SEQ ID NO 9
<211> LENGTH: 26
<212> TYPE: DNA
<213> ORGANISM: Burkholderia

<400> SEQUENCE: 9

tgccattgcc ctgtcatttg ccgcag                                          26


<210> SEQ ID NO 10
<211> LENGTH: 26
```

-continued

<212> TYPE: DNA
<213> ORGANISM: Burkholderia

<400> SEQUENCE: 10
acaactgact gaacagactc aggtcg 26

<210> SEQ ID NO 11
<211> LENGTH: 26
<212> TYPE: DNA
<213> ORGANISM: Rickettsia

<400> SEQUENCE: 11
gcttatttta gaggttatag agttcg 26

<210> SEQ ID NO 12
<211> LENGTH: 26
<212> TYPE: DNA
<213> ORGANISM: Rickettsia

<400> SEQUENCE: 12
acttcttgag gtaaaagtaa agctct 26

<210> SEQ ID NO 13
<211> LENGTH: 24
<212> TYPE: DNA
<213> ORGANISM: Coxiella

<400> SEQUENCE: 13
cccaacgaaa ccttgcgtga ggca 24

<210> SEQ ID NO 14
<211> LENGTH: 24
<212> TYPE: DNA
<213> ORGANISM: Coxiella

<400> SEQUENCE: 14
cccaacgaaa ccttgcgtga ggca 24

<210> SEQ ID NO 15
<211> LENGTH: 26
<212> TYPE: DNA
<213> ORGANISM: Brucella

<400> SEQUENCE: 15
cgatggcgtc atccatgtgc tgggtg 26

<210> SEQ ID NO 16
<211> LENGTH: 26
<212> TYPE: DNA
<213> ORGANISM: Brucella

<400> SEQUENCE: 16
agtttgagca tgatgccgac gaaagc 26

<210> SEQ ID NO 17
<211> LENGTH: 26
<212> TYPE: DNA
<213> ORGANISM: Escherichia

<400> SEQUENCE: 17
gcaggcctga actcatcgtc ggatga 26

<210> SEQ ID NO 18
<211> LENGTH: 25

-continued

<212> TYPE: DNA
<213> ORGANISM: Escherichia

<400> SEQUENCE: 18
tcatcccaat acgagcggtc gctgg 25

<210> SEQ ID NO 19
<211> LENGTH: 25
<212> TYPE: DNA
<213> ORGANISM: Variola virus

<400> SEQUENCE: 19
gcagcaccgt atacaccacc caatg 25

<210> SEQ ID NO 20
<211> LENGTH: 27
<212> TYPE: DNA
<213> ORGANISM: Variola virus

<400> SEQUENCE: 20
acgtctccaa cagacgtgtg tccggat 27

<210> SEQ ID NO 21
<211> LENGTH: 24
<212> TYPE: DNA
<213> ORGANISM: Machupo virus

<400> SEQUENCE: 21
cattcatcat gtctaaagca atgc 24

<210> SEQ ID NO 22
<211> LENGTH: 25
<212> TYPE: DNA
<213> ORGANISM: Machupo virus

<400> SEQUENCE: 22
ggctgtgaag cctaaagtgg tgaga 25

<210> SEQ ID NO 23
<211> LENGTH: 24
<212> TYPE: DNA
<213> ORGANISM: Eastern equine encephalomyelitis virus

<400> SEQUENCE: 23
tacttgtctg cggcgccttg ggcg 24

<210> SEQ ID NO 24
<211> LENGTH: 22
<212> TYPE: DNA
<213> ORGANISM: Eastern equine encephalomyelitis virus

<400> SEQUENCE: 24
cgcagaagca gtaggctcct cc 22

<210> SEQ ID NO 25
<211> LENGTH: 26
<212> TYPE: DNA
<213> ORGANISM: Influenza

<400> SEQUENCE: 25
accatttgaa tggatgtcaa tccgac 26

<210> SEQ ID NO 26
<211> LENGTH: 26

-continued

<212> TYPE: DNA
<213> ORGANISM: Influenza

<400> SEQUENCE: 26
gactgtgtcc atggtgtatc ctgttc 26

<210> SEQ ID NO 27
<211> LENGTH: 20
<212> TYPE: DNA
<213> ORGANISM: Venezuelan equine encephalitis virus

<400> SEQUENCE: 27
gttagttgcg acgggtacgt 20

<210> SEQ ID NO 28
<211> LENGTH: 21
<212> TYPE: DNA
<213> ORGANISM: Venezuelan equine encephalitis virus

<400> SEQUENCE: 28
gcagcacaag aatccctcgc g 21

<210> SEQ ID NO 29
<211> LENGTH: 20
<212> TYPE: DNA
<213> ORGANISM: Lassa virus

<400> SEQUENCE: 29
atcctgggtg accacttcat 20

<210> SEQ ID NO 30
<211> LENGTH: 26
<212> TYPE: DNA
<213> ORGANISM: Lassa virus

<400> SEQUENCE: 30
gcaatagaac tgggtgcatg ggtctt 26

<210> SEQ ID NO 31
<211> LENGTH: 24
<212> TYPE: DNA
<213> ORGANISM: Rift Valley fever virus

<400> SEQUENCE: 31
atgagtgcac tgctcagtac gcca 24

<210> SEQ ID NO 32
<211> LENGTH: 26
<212> TYPE: DNA
<213> ORGANISM: Rift Valley fever virus

<400> SEQUENCE: 32
gcaaggctca actctctgga tgggct 26

<210> SEQ ID NO 33
<211> LENGTH: 26
<212> TYPE: DNA
<213> ORGANISM: Ebola virus

<400> SEQUENCE: 33
gcaattgcac tcggagtcgc cacagc 26

<210> SEQ ID NO 34
<211> LENGTH: 26

-continued

<212> TYPE: DNA
<213> ORGANISM: Ebola virus

<400> SEQUENCE: 34
cacttgtttt gggcagtgac gcagca 26

<210> SEQ ID NO 35
<211> LENGTH: 25
<212> TYPE: DNA
<213> ORGANISM: Junin virus

<400> SEQUENCE: 35
acctctgatc cagacatgca gtcga 25

<210> SEQ ID NO 36
<211> LENGTH: 24
<212> TYPE: DNA
<213> ORGANISM: Junin virus

<400> SEQUENCE: 36
aaacaggtga gaagtcaagg tgct 24

<210> SEQ ID NO 37
<211> LENGTH: 25
<212> TYPE: DNA
<213> ORGANISM: Marburg virus

<400> SEQUENCE: 37
gaagttgcta gtttcaagca ggcgt 25

<210> SEQ ID NO 38
<211> LENGTH: 25
<212> TYPE: DNA
<213> ORGANISM: Marburg virus

<400> SEQUENCE: 38
tttctcgttt ctggctgagg acggc 25

<210> SEQ ID NO 39
<211> LENGTH: 26
<212> TYPE: DNA
<213> ORGANISM: Yellow fever virus

<400> SEQUENCE: 39
ctaagctgtg aggcagtgca ggctgg 26

<210> SEQ ID NO 40
<211> LENGTH: 26
<212> TYPE: DNA
<213> ORGANISM: Yellow fever virus

<400> SEQUENCE: 40
aggtctgctt attcttgagc aaactg 26

<210> SEQ ID NO 41
<211> LENGTH: 24
<212> TYPE: DNA
<213> ORGANISM: Crimean-Congo virus

<400> SEQUENCE: 41
aattccctca taaggtgtgc caat 24

<210> SEQ ID NO 42
<211> LENGTH: 24

-continued

```
<212> TYPE: DNA
<213> ORGANISM: Crimean-Congo virus

<400> SEQUENCE: 42

aattccctca taaggtgtgc caat                                          24


<210> SEQ ID NO 43
<211> LENGTH: 28
<212> TYPE: DNA
<213> ORGANISM: Dengue virus

<400> SEQUENCE: 43

tcaatatgct gaaacgcgag agaaaccg                                      28


<210> SEQ ID NO 44
<211> LENGTH: 29
<212> TYPE: DNA
<213> ORGANISM: Dengue virus

<400> SEQUENCE: 44

ttgcaccaac agtcaatgtc ttcaggttc                                     29
```